United States Patent
Jensen

(10) Patent No.: US 9,901,382 B2
(45) Date of Patent: Feb. 27, 2018

(54) BONE GRAFT INJECTOR DEVICE

(71) Applicant: Wade K. Jensen, Dakota Dunes, SD (US)

(72) Inventor: Wade K. Jensen, Dakota Dunes, SD (US)

(*) Notice: Subject to any disclaimer, the term of this patent is extended or adjusted under 35 U.S.C. 154(b) by 374 days.

(21) Appl. No.: 14/713,669

(22) Filed: May 15, 2015

(65) Prior Publication Data

US 2016/0331429 A1    Nov. 17, 2016

(51) Int. Cl.
  *A61B 17/88* (2006.01)
  *A61M 5/31* (2006.01)
  *A61F 2/46* (2006.01)

(52) U.S. Cl.
  CPC ........ *A61B 17/8825* (2013.01); *A61F 2/4601* (2013.01)

(58) Field of Classification Search
  CPC ........... A61B 17/8816; A61B 17/8825; A61M 2005/31521; A61M 5/31513
  See application file for complete search history.

(56) References Cited

U.S. PATENT DOCUMENTS

| | | | |
|---|---|---|---|
| 4,801,263 A | 1/1989 | Clark | |
| 6,530,896 B1 | 3/2003 | Elliot | |
| 8,092,464 B2 | 1/2012 | McKay | |
| 8,128,591 B2 | 3/2012 | Simonton et al. | |
| 8,685,031 B2 | 4/2014 | Kleiner et al. | |
| 2007/0026030 A1 | 2/2007 | Gill et al. | |
| 2007/0233149 A1* | 10/2007 | Bohner | A61B 17/8816 606/93 |
| 2008/0009823 A1* | 1/2008 | McKay | A61B 17/7044 604/500 |
| 2010/0016807 A1 | 1/2010 | Thilly | |
| 2012/0078315 A1* | 3/2012 | Sweeney | A61B 17/8811 606/86 A |
| 2012/0130164 A1* | 5/2012 | Palese | A61B 17/52 600/104 |

FOREIGN PATENT DOCUMENTS

WO    WO2013112666    8/2013

* cited by examiner

*Primary Examiner* — Zade Coley
*Assistant Examiner* — Olivia C Chang

(57) ABSTRACT

A bone graft injector device for injecting bone graft material during a surgical procedure includes a barrel defining a channel extending between a first end and a second end. The second end of the barrel defines an opening into the channel. A matter holding section of the channel extending inwardly from the opening has a constant cross-sectional area extending towards the first end. The constant cross-sectional area is equal to an area of the opening. A plunger is positioned in the channel wherein the plunger is configured for urging bone graft material within the matter holding section of the channel out of the second end through the opening.

11 Claims, 4 Drawing Sheets

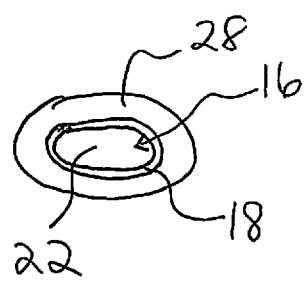

BONE GRAFT INJECTOR DEVICE

BACKGROUND OF THE DISCLOSURE

Field of the Disclosure

The disclosure relates to injector devices and more particularly pertains to a new injector device for injecting bone graft material during a surgical procedure.

SUMMARY OF THE DISCLOSURE

An embodiment of the disclosure meets the needs presented above by generally comprising a barrel defining a channel extending between a first end and a second end. The second end of the barrel defines an opening into the channel. A matter holding section of the channel extending inwardly from the opening has a constant cross-sectional area extending towards the first end. The constant cross-sectional area is equal to an area of the opening. A plunger is positioned in the channel wherein the plunger is configured for urging bone graft material within the matter holding section of the channel out of the second end through the opening.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 5 is a bottom view of an embodiment of the disclosure.

DESCRIPTION OF THE PREFERRED EMBODIMENT

Figure 1:
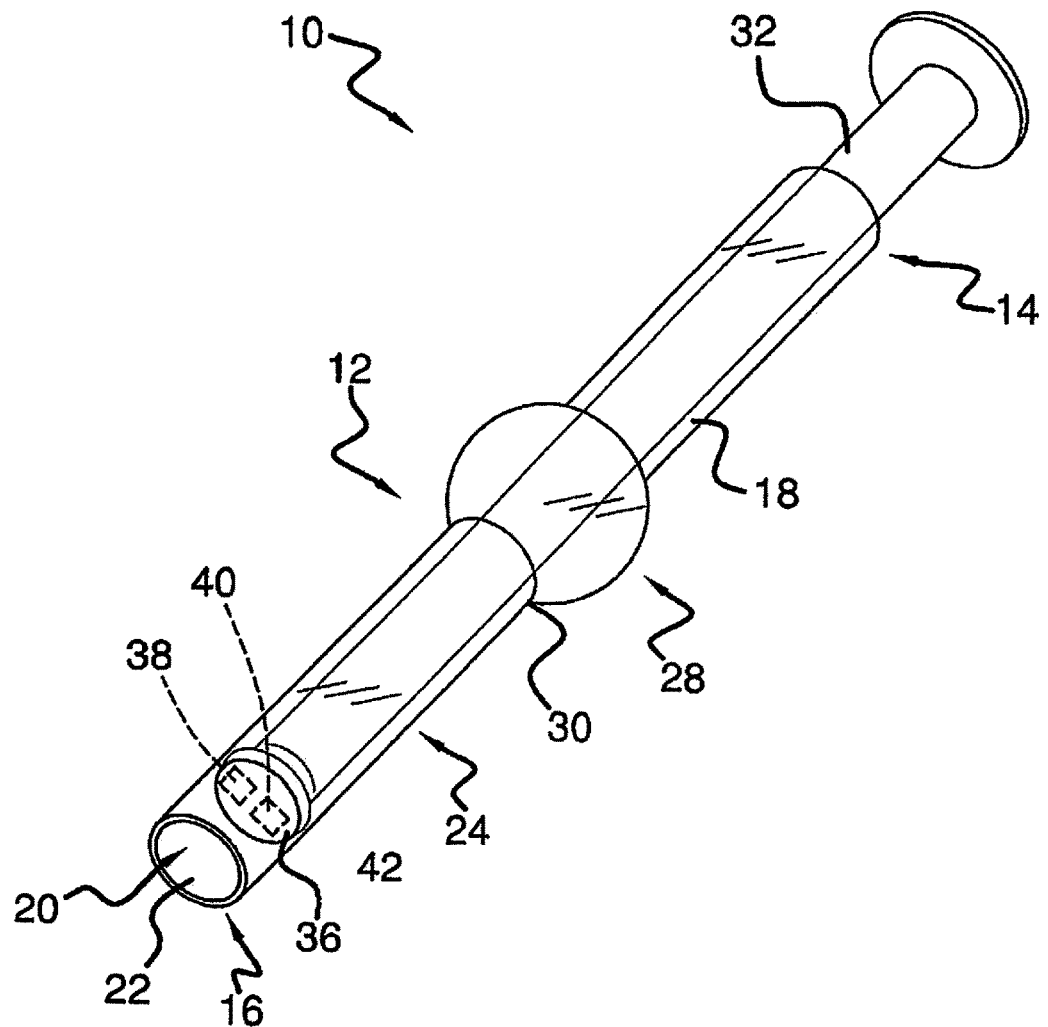
FIG. 1 is a bottom front side perspective view of a bone graft injector device according to an embodiment of the disclosure.

With reference now to the drawings, and in particular to FIGS. 1 through 5 thereof, a new injector device embodying the principles and concepts of an embodiment of the disclosure and generally designated by the reference numeral 10 will be described.

Figure 2:
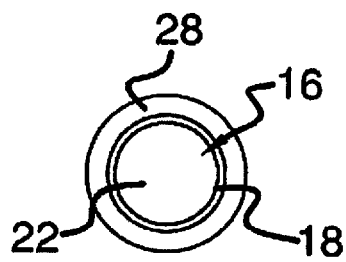
FIG. 2 is a bottom view of an embodiment of the disclosure.
Figure 3:
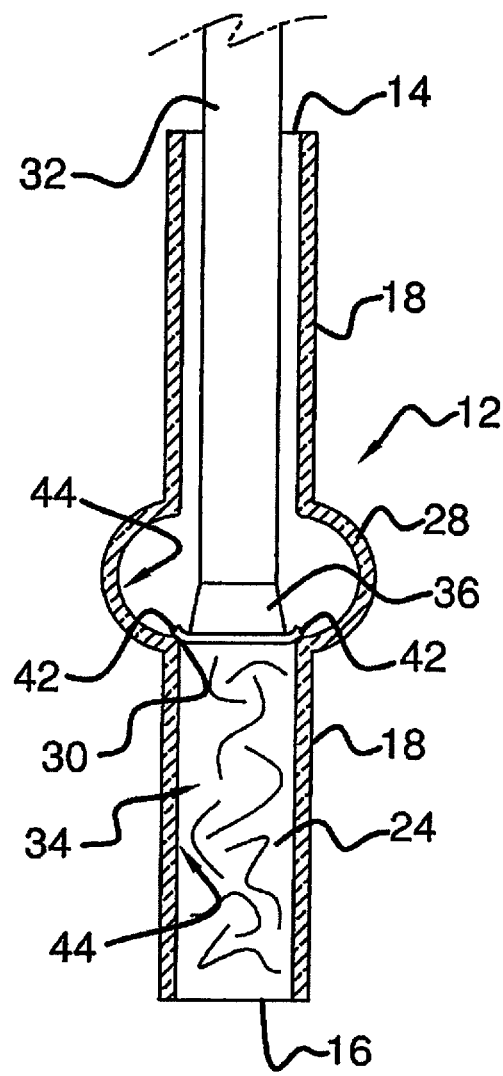
FIG. 3 is a partial cut-away front view of an embodiment of the disclosure.
Figure 4:
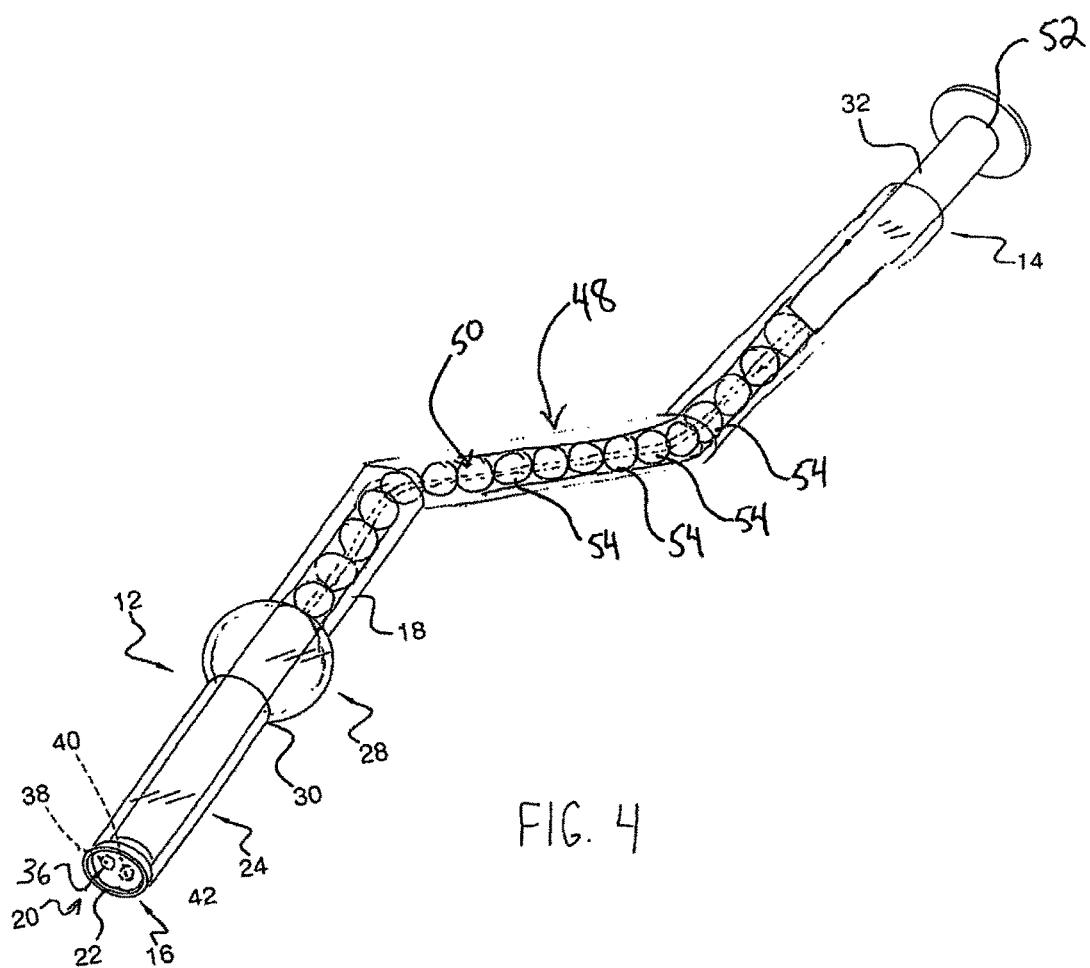
FIG. 4 is a bottom front side perspective view of an embodiment of the disclosure.

As best illustrated in FIGS. 1 through 5, the bone graft injector device 10 generally comprises a barrel 12 having a first end 14 and a second end 16. The barrel 12 is straight as shown in FIGS. 1 through 3. As shown in FIG. 4, and described more fully below, the barrel 12 may have an offset.

The barrel 12 is formed by a wall 18 having a constant thickness extending between the first end 14 and the second end 16 wherein the barrel 12 defines an interior channel 20 extending between the first end 14 and the second end 16. The second end 16 of the barrel 12 defines an opening 22 into the channel 20. A matter holding section 24 of the channel 20 extends inwardly from the second end 16 towards the first end 14. The matter holding section 24 has a constant cross-sectional area extending from the opening 22 towards the first end 14. The constant cross-sectional area is equal to an area of the opening 22. The opening 22 has a size between 3 square millimeters and 80 square millimeters permitting the insertion of bone graft material 34 into the matter holding section 24 of the channel 20 through the opening 22. A length of the barrel is between 12 centimeters long and 36 centimeters in length allowing for an extended reach into a body cavity compared to commonly sized syringes currently found in operating rooms. As shown in FIG. 5, the barrel 12 may have an oval transverse cross-sectional shape relative to a longitudinal axis of the barrel 12 facilitating insertion of the barrel 12 into the body cavity through an incision. The channel 20 has a bulbous medial section 28 between the first end 14 and the second end 16. The bulbous medial section 28 is positioned at a distal end 30 of the matter holding section 24 relative to the opening 22.

A plunger 32 is positioned in the channel 20 wherein the plunger 32 is configured for urging bone graft material 34 within the matter holding section 24 of the channel 20 out of the second end 16 through the opening 22. The plunger 32 has a head 36 positioned in the channel 20. The head 36 may be constructed of rubber or the like. The plunger 32 may be constructed of a surgical grade plastic or the like. A radiolucent marker 38 may be coupled to the head 36 of the plunger 32 to facilitate locating the head 36 in the event the head 36 becomes dislodged from the plunger 32 inside the body cavity. A magnetically attractable material 40 such as a sufficient amount of a metal may be coupled to the head 36 of the plunger 32 wherein the head 36 is configured for being retrieved from an interior cavity of a patient by using a magnet to attract and couple the head 36 to the magnet. Each of the radiolucent marker 38 and the magnetically attractable material 40 may be formed having rounded edges to minimize potential injury to the patient if dislodged or uncoupled from the head 36.

A peripheral flange 42 extends outwardly around the head 36 of the plunger 32. The peripheral flange 42 is resiliently flexible and abuts an interior surface 44 of the channel 20 to facilitate urging the bone graft material 34 through the barrel 12. An interior diameter of the channel 20 in the medial bulbous section 28 is greater than a diameter of the peripheral flange 42 extending from the head 36 of the plunger 32. The interior diameter of the channel 20 in the medial bulbous section 28 tapers approaching the matter holding section 24 such that the peripheral flange 42 is free from contacting the barrel 12 in the medial bulbous section 28 but engages the interior surface 44 of the channel 20 in the matter holding section 24 folding the peripheral flange 42 back towards the first end 14 of the barrel 12 as the head 36 of the plunger 32 is urged into the matter holding section 24.

FIG. 4 discloses an embodiment in which the barrel 12 includes an offset section 48 between the first end 14 and the second end 16. The offset section 48 is positioned between the first end 14 and the bulbous medial section 28. In the embodiment shown in FIG. 4, the plunger 32 includes a flexible section 50 positioned between the head 36 and a distal end 52 of the plunger 32 relative to the head 36. The flexible section 50 is positioned to extend through the offset section 48 and is incompressible along a longitudinal axis of the plunger 32 such that the flexible section 48 transfers pressure through the offset section 48 such that pressing on the distal end 52 urges the plunger 32 through the barrel 12 including the offset section 48 to dispense the bone graft material 34 from the matter holding section 24. Thus, the embodiment shown in FIG. 4 works in the same manner but allows for different angling of the second end 16 of the barrel 12 as may be needed or desired for dispensing the bone graft material 36 from the matter holding section 24. The flexible section 48 may be formed by a plurality of spheres 54 linearly arranged and interconnected in a conventional manner allowing for pivoting of adjacently positioned spheres 54 wherein the plunger 32 translates linear force exerted on the distal end 52 of the plunger 32 to the head 36. Each of the spheres 54 is sized to be complementary to a diameter of the interior channel 20 extending through the barrel 12.

In use, the head 36 of the plunger 32 is positioned within the barrel 12 such that the head 36 is positioned in a desired position spaced from the second end 16 of the barrel 12 and the bone graft material 34 is loaded into the matter holding section 24 through the opening 22 in the second end 16. The second end 16 is inserted into the patient through an incision and placed in a desired position to dispense the bone graft material 34 from the barrel 12 by exerting pressure on the plunger 32.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A bone graft injector device comprising:
a barrel having a first end and a second end, said barrel defining an interior channel extending between said first end and said second end, said second end of said barrel defining an opening into said channel, a matter holding section of said channel extending inwardly from said opening having a constant cross-sectional area extending towards said first end, said constant cross-sectional area being equal to a cross-sectional area of said opening, said channel having a bulbous medial section between said first end and said second end, said bulbous medial section being positioned at a distal end of said matter holding section relative to said opening; and a plunger positioned in said channel wherein said plunger is configured for urging bone graft material within said matter holding section of said channel out of said second end through said opening, said plunger having a head positioned in said channel; and
a peripheral flange extending outwardly around said head of said plunger, said peripheral flange being resiliently flexible, an interior diameter of said channel in said medial bulbous section being greater than a diameter of said peripheral flange extending from said head of said plunger, said interior diameter of said channel in said medial bulbous section tapering approaching said matter holding section such that said peripheral flange engages an interior surface of said channel and folds back towards said first end of said barrel as said head of said plunger is urged into said matter holding section.

2. The device of claim 1, wherein said cross-sectional area of said opening is between 3 square millimeters and 80 square millimeters.

3. The device of claim 1, further comprising said barrel having an oval transverse cross-sectional shape relative to a longitudinal axis of said barrel.

4. The device of claim 1, further comprising a radiolucent marker coupled to a head of said plunger.

5. The device of claim 1, further comprising a magnetically attractable material coupled to a head of said plunger wherein said head is configured for being retrieved from an interior cavity of a patient using a magnet.

6. The device of claim 1, further comprising a length of said barrel being between 12 centimeters long and 36 centimeters in length.

7. The device of claim 1, further comprising said barrel being straight.

8. The device of claim 1, further comprising said barrel including an offset section between said first end and said second end.

9. The device of claim 1, further comprising said barrel including an offset section between said first end and said second end, said offset section being positioned between said first end of said barrel and said bulbous medial section of said channel.

10. The device of claim 9, further comprising said plunger having a flexible section positioned to extend through said offset section of said barrel.

11. A bone graft injector device comprising:
a barrel having a first end and a second end, said barrel being straight, said barrel being formed by a wall having a constant thickness extending between said first end and said second end wherein said barrel defines an interior channel extending between said first end and said second end, said second end of said barrel defining an opening into said channel, a matter holding section of said channel extending inwardly from said opening having a constant cross-sectional area extending towards said first end, said constant cross-sectional area being equal to a cross-sectional area of said opening, a length of said barrel being between 12 centimeters long and 36 centimeters in length, said cross-sectional area of said opening being between 3 square millimeters and 80 square millimeters, said barrel having an oval transverse cross-sectional shape relative to a longitudinal axis of said barrel, said channel having a bulbous medial section between said first end and said second end, said bulbous medial section being positioned at a distal end of said matter holding section relative to said opening;

a plunger positioned in said channel wherein said plunger is configured for urging bone graft material within said matter holding section of said channel out of said second end through said opening, said plunger having a head positioned in said channel;

a peripheral flange extending outwardly around said head of said plunger, said peripheral flange being resiliently flexible, an interior diameter of said channel in said medial bulbous section being greater than a diameter of said peripheral flange extending from said head of said plunger, said interior diameter of said channel in said medial bulbous section tapering approaching said matter holding section such that said peripheral flange engages an interior surface of said channel and folds back towards said first end of said barrel as said head of said plunger is urged into said matter holding section;

a radiolucent marker coupled to a head of said plunger; and a magnetically attractable material coupled to a head of said plunger wherein said head is configured for being retrieved from an interior cavity of a patient using a magnet.

* * * * *